United States Patent
Lee

(10) Patent No.: US 10,507,800 B2
(45) Date of Patent: Dec. 17, 2019

(54) SENSOR FOR VEHICLE, SENSING METHOD THEREOF AND VEHICLE SYSTEM

(71) Applicant: LG INNOTEK CO., LTD., Seoul (KR)

(72) Inventor: Gyu Rin Lee, Seoul (KR)

(73) Assignee: LG Innotek Co., Ltd., Seoul (KR)

( * ) Notice: Subject to any disclaimer, the term of this patent is extended or adjusted under 35 U.S.C. 154(b) by 173 days.

(21) Appl. No.: 15/547,386

(22) PCT Filed: Sep. 24, 2015

(86) PCT No.: PCT/KR2015/010139
§ 371 (c)(1),
(2) Date: Jul. 28, 2017

(87) PCT Pub. No.: WO2016/125975
PCT Pub. Date: Aug. 11, 2016

(65) Prior Publication Data
US 2018/0022320 A1 Jan. 25, 2018

(30) Foreign Application Priority Data
Feb. 6, 2015 (KR) .......... 10-2015-0018547

(51) Int. Cl.
*G01R 27/26* (2006.01)
*B60S 1/08* (2006.01)
(Continued)

(52) U.S. Cl.
CPC ............ *B60S 1/0825* (2013.01); *G01N 27/22* (2013.01); *G01N 27/221* (2013.01); *G01N 27/226* (2013.01); *G01R 17/16* (2013.01); *G01R 27/26* (2013.01); *G01R 27/2605* (2013.01); *H05B 3/145* (2013.01); *H05B 3/84* (2013.01); *H05B 3/845* (2013.01); *H05B 2203/002* (2013.01);
(Continued)

(58) Field of Classification Search
CPC .... G01N 27/22; G01N 27/221; G01N 27/226; G01R 27/2605; G01R 27/26; G01R 17/16
USPC ... 324/76.11–76.83, 459, 600, 649, 658, 663
See application file for complete search history.

(56) References Cited

U.S. PATENT DOCUMENTS

2010/0163675 A1   7/2010  Rashid et al.
2015/0109244 A1*  4/2015  Jang ................. G06F 3/0416
                                                    345/174

(Continued)

FOREIGN PATENT DOCUMENTS

JP    S57-157148    9/1982
JP    S57-160052    10/1982
(Continued)

OTHER PUBLICATIONS

JPH05264496 machine translation, Oct. 12, 1993.*
(Continued)

*Primary Examiner* — Raul J Rios Russo
(74) *Attorney, Agent, or Firm* — KED & Associates, LLP

(57) ABSTRACT

According to one embodiment, there is provided a sensor for a vehicle, which includes: a vehicle glass; a substrate disposed on the vehicle glass; a transparent sensing electrode disposed on the substrate; and a wire electrode connected to the sensing electrode, wherein the sensing electrode comprises a first sensing electrode and a second sensing electrode spaced apart from the first sensing electrode.

14 Claims, 11 Drawing Sheets

(51) Int. Cl.
*G01N 27/22* (2006.01)
*G01R 17/16* (2006.01)
*H05B 3/84* (2006.01)
*H05B 3/14* (2006.01)

(52) U.S. Cl.
CPC .... *H05B 2203/013* (2013.01); *H05B 2214/04* (2013.01)

(56) References Cited

U.S. PATENT DOCUMENTS

| | | | | |
|---|---|---|---|---|
| 2015/0338971 A1* | 11/2015 | Nam | ........................ | G06F 3/044 345/174 |
| 2016/0202804 A1* | 7/2016 | Park | ........................ | G06F 3/044 345/174 |
| 2017/0228067 A1* | 8/2017 | Kim | ........................ | G06F 3/044 |
| 2018/0203549 A1* | 7/2018 | Kim | ........................ | G06F 3/041 |
| 2018/0267639 A1* | 9/2018 | Han | ........................ | G06F 3/041 |

FOREIGN PATENT DOCUMENTS

| | | |
|---|---|---|
| JP | H05-264496 | 10/1993 |
| JP | H09-127260 | 5/1997 |

OTHER PUBLICATIONS

International Search Report and Written Opinion dated Jan. 13, 2016 issued in Application No. PCT/KR2015/010139 (Full English Text).

\* cited by examiner

SENSOR FOR VEHICLE, SENSING METHOD THEREOF AND VEHICLE SYSTEM

CROSS-REFERENCE TO RELATED PATENT APPLICATIONS

This application is a U.S. National Stage application under 35 U.S.C. § 371 of PCT Application No. PCT/KR2015/010139, filed Sep. 24, 2015, which claims priority to Korean Patent Application No. 10-2015-0018547, filed Feb. 6, 2015, whose entire disclosures are hereby incorporated by reference.

TECHNICAL FIELD

The embodiment relates to a sensor for a vehicle, a sensing method thereof and a vehicle system.

BACKGROUND ART

In recent years, the technical trend of automobile industry has been focused on developments of digitalizing each system for the purpose of driver's convenience over the previous mechanical aspect such as an engine In detail, as one example of digitalizing an automobile, there is a technique on a vehicle rain sensor for automatically controlling a vehicle wiper according to an amount of rainfall. Even though a driver does not manually operate a wiper during raining, such a rain sensor senses an amount of rainfall to automatically control the operation of the wiper, so that the driver's convenience may be improved.

As one example of the vehicle rain sensor, there is an optical rain sensor in which a light emitting unit and the light receiving unit are installed at an inside of the front glass of a vehicle and an amount of rainfall is determined by using an variation of intensity of light received by the light receiving unit due to the variation of a light refractive index by rain drops. However, according to the optical rain sensor of the related art, since the structure and the installation are complex and the components are expensive, the producing cost is increased. In addition, the measuring area is small and influenced by various kinds of contaminants, so that the accuracy may be degraded.

In addition, as another example, there is a vehicle rain sensor of determining whether it is raining and an amount of rain drops by measuring the wire impedance varied with the raindrop on a wire disposed inside the windshield glass of a vehicle. However, in case of the vehicle rain sensor, the wire is viewed so that the driver's sight may be disturbed, so that the size and position may be limited.

Meanwhile, since a mist on a vehicle windshield glass is an interrupting element of driving, a driver must operate an air conditioner or a hot-wire during driving to remove the mist from the surface of a vehicle windshield glass, so that the driver's concentration on driving may be disturbed.

DISCLOSURE

Technical Problem

The embodiment is to provide a sensor for a vehicle, which is capable of exactly measuring a raindrop or a mist on a vehicle window, a sensing method thereof, a vehicle system including the same and a control method thereof.

Technical Solution

According to one embodiment, there is provided a sensor for a vehicle, which includes: a vehicle glass; a substrate disposed on the vehicle glass; a transparent sensing electrode disposed on the substrate; and a wire electrode connected to the sensing electrode, wherein the sensing electrode comprises a first sensing electrode and a second sensing electrode spaced apart from the first sensing electrode.

The first sensing electrode may extend in a first direction, and the second sensing electrode extends in a second direction, and the sensor may further include an insulating material interposed between the first and second sensing electrodes.

In addition, each of the first and second sensing electrodes may include a plurality of electrode patterns, and the electrode patterns of the first sensing electrode are spaced apart from the electrode patterns of the second sensing electrode.

In addition, the glass of the vehicle may include at least one of a front glass of the vehicle, a side glass of the vehicle, a rear glass of the vehicle and a side mirror.

In addition, the glass of the vehicle may include an outer glass and an inner glass disposed on the outer glass, and the transparent substrate is interposed between the outer and inner glasses.

In addition, the transparent substrate may make direct contact with top and bottom surfaces of the glass of the vehicle.

In addition, the sensor may further include a control unit including a driving unit and a sensing unit, wherein the driving unit of the control unit applies a driving signal to the second sensing electrode, and the sensing unit of the control unit receives a variation of capacitance through the first sensing electrode.

In addition, the sensing electrode may sense a raindrop provided on the top surface of the glass of the vehicle based on a variation of capacitance.

In addition, the sensing electrode may sense dew provided on a bottom surface of the glass of the vehicle based on a variation of capacitance.

In addition, the sensing electrode may serve as a hot-wire electrode.

According to another embodiment, there is provided a sensing method of a sensor of a vehicle which includes first and second sensing electrode and is disposed on a vehicle glass to sense a raindrop. The sensing method includes setting a capacitance reference value; comparing a capacitance value sensed by the sensing electrode with the capacitance reference value; determining that the raindrop is formed on the vehicle glass when a difference between the capacitance reference value and the sensed capacitance value exceeds a preset first reference variation value; and measuring an amount of rainfall based on the capacitance variation.

In addition, the measuring step may measure the amount of rainfall based on areas of the first and second sensing electrodes.

In addition, when the difference between the capacitance reference value and the sensed capacitance value is less than the first reference variation value and exceeds a preset second reference variation value, the sensing method may further include a step of operating an operation as a case that dew is formed on the vehicle glass.

In addition, the sensing method may further include the step of removing the dew by generating heat by applying electric power to the first and second sensing electrodes.

According to still another embodiment, there is provided a vehicle system which includes: a sensor for a vehicle including a sensing electrode; a control unit to receive a raindrop or dew sensing signal from the sensor; and a wiper, a vehicle hot-wire or an air conditioner operated by an instruction of the control unit, wherein the control unit receives a variation of capacitance from the sensing electrode through the raindrop or dew sensing signal and operates the wiper or the vehicle hot-wire according to the sensing signal.

Advantageous Effects

According to the embodiment, the sensor for a vehicle may exactly sense dew or a raindrop on a vehicle glass based on the variation of capacitance.

In addition, the sensor for a vehicle according to the embodiment is transparent, so that the driver's sight is not disturbed wherever the sensor is installed in the vehicle.

In addition, the sensor for a vehicle has a single-layered structure, so that the sensor may be formed to have a thin thickness. When the sensor for a vehicle is embedded in a vehicle glass, a raindrop and dew may be sensed at the same time.

In addition, the sensor for a vehicle may measure an amount of rainfall based on an area in which capacitance is varied.

In addition, the sensor for a vehicle may measure a degree of turbidity of a vehicle glass due to moisture based on a value of varied capacitance. In this case, the control unit may more exactly measure the degree of turbidity of a vehicle glass due to moisture based on a gradient of the variation of capacitance.

In addition, the sensor for a vehicle may remove dew by using the sensing electrode as a hot-wire.

In addition, the sensor for a vehicle may exactly measure an amount of dew generated due to moisture through the sensing electrode and remove the dew by using the sensing electrode as a hot-wire.

In addition, according to the vehicle system of an embodiment, the transparent sensor is suitably disposed at a position required by a vehicle, so that the vehicle system may exactly measure information required to secure driver's sight. In addition, driver's convenience may be improved by suitably controlling a wiper or hot-wire based on the information collected by the sensor for a vehicle.

MODE FOR INVENTION

Figure 1:
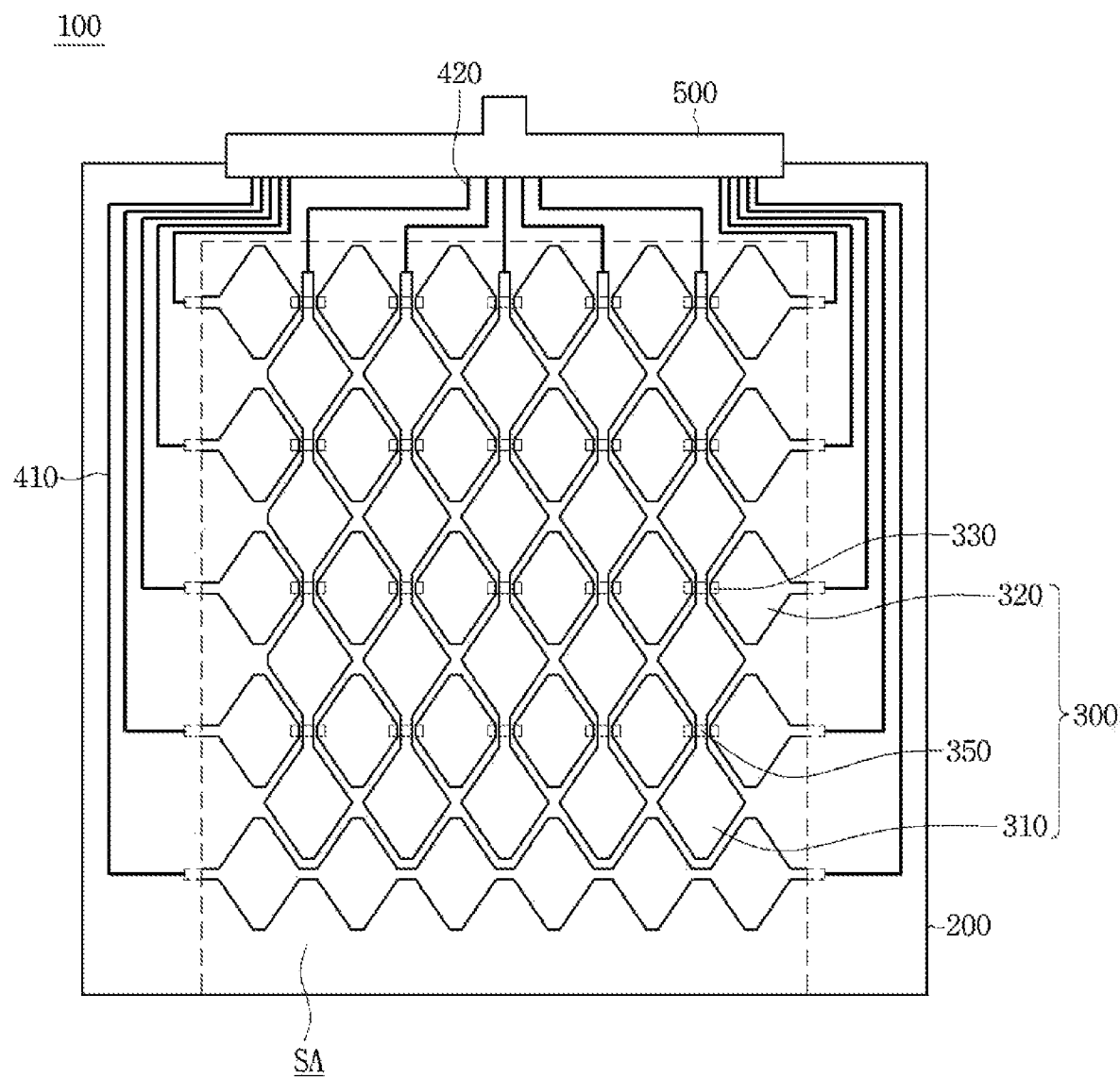
FIG. 1 is a plan view showing a sensor for a vehicle according to one embodiment.

In the description of the embodiments, it will be understood that, when a layer (or film), a region, a pattern, or a structure is referred to as being "on" or "under" another substrate, another layer (or film), another region, another pad, or another pattern, it can be "directly" or "indirectly" on the other substrate, layer (or film), region, pad, or pattern, or one or more intervening layers may also be present. Such a position of the layer has been described with reference to the drawings.

In the following description, when a part is connected to the other part, the parts are not only directly connected to each other, but also indirectly connected to each other while interposing another part therebetween. In addition, when a predetermined part "includes" a predetermined component, the predetermined part does not exclude other components, but may further include other components unless otherwise indicated.

The thickness and size of each layer (film), region, pattern, or structure shown in the drawings may be exaggerated, omitted or schematically drawn for the purpose of convenience or clarity. In addition, the size of each layer (film), region, pattern, or structure does not utterly reflect an actual size.

Hereinafter, embodiments will be described with reference to accompanying drawings.

A vehicle may include an automobile, a ship, an airplane, a motorcycle and a train. Although the following embodiments will be described based on an automobile for the purpose of convenience, the embodiments may be applied to all vehicles.

FIG. 1 is a plan view showing a sensor for a vehicle according to an embodiment.

Referring to FIG. 1, a sensor 100 for a vehicle according to an embodiment may include a substrate 200, a sensing electrode 300 and a wire electrode 400. The sensing electrode 300 may include first and second sensing electrode 310 and 320.

The substrate 200 may be rigid or flexible.

The substrate 200 may be rigid or flexible. For example, the protective substrate 100 may include glass or plastic. In detail, the substrate 200 may include chemically tempered/half-tempered glass such as soda lime glass or aluminosilicate glass, reinforced or flexible plastic such as polyimide (PI), polyethylene terephthalate (PET), propylene glycol (PPG), or polycarbonate (PC), or sapphire. The sapphire has superior electric characteristics, such as permittivity, so that the sapphire has the advantages of a superior response speed to a raindrop and superior surface strength.

In addition, the substrate 200 may include an optically isotropic film. For example, the substrate 100 may include cyclic olefin copolymer (COC), cyclic olefin polymer (COP), optically isotropic polycarbonate (PC), or optically isotropic polymethyl methacrylate (PMMA).

In addition, the substrate 200 may be bent to have a partial curved surface. That is, the substrate 200 may be bent to have a partial flat surface and a partial curved surface. In detail, an end of the substrate 200 may be bent to have a curved surface or may be bent or flexed to have a surface including a random curvature.

In addition, the substrate 200 may include a flexible substrate having a flexible property. The substrate 200 may include a curved or bended substrate 200.

The sensing and wire electrodes 300 and 400 and a printed circuit board 500 may be disposed on the substrate 200. That is, the substrate 200 may serve as a support substrate.

The substrate 200 may include a vehicle glass. For example, the substrate 200 may be a front glass, a side glass, a rear glass or a side mirror of a vehicle. That is, the sensing and wire electrodes 300 and 400 and the printed circuit board 500 may be supported by the vehicle glass.

Alternatively, an additional vehicle glass may be disposed on the substrate 200. That is, the sensing and wire electrodes 300 and 400 and the printed circuit board 500 may be supported by the substrate 200 and combined with (adhere to) each other through an adhesive layer.

The substrate 200 may have a sensing area SA defined therein. The sensing area SA may sense a mist thereon.

In detail, the sensing electrode 300 may be disposed on the sensing area SA of the substrate 200. The sensing electrode 300 may include first and second sensing electrodes 310 and 320.

The first sensing electrode 310 may be disposed on the substrate 200 while extending in a first direction. In this case, the first sensing electrode 310 may make direct contact with the substrate 200.

The second sensing electrode 320 may be disposed on the substrate 200 while extending in a second direction. In detail, the second sensing electrode 320 may extend in a direction different from the first direction and may make direct contact with the substrate 200. That is, the first and second sensing electrodes 310 and 320 may make direct contact with the substrate and extend in mutually different directions on the same surface of the substrate 200.

Thus, all sensing electrodes 300 according to the embodiment may have a single-layer structure formed on the same surface. When the sensor for a vehicle having the single-layer structure is disposed on the vehicle glass, the sensor may sense raindrops on upper and lower surfaces of the glass at the same time.

The first and second sensing electrodes 310 and 320 may be disposed on the substrate 200 while being insulated from each other.

In detail, a bridge electrode 330 may be disposed on one surface of the substrate 200, on which the sensing electrode 300 is disposed. For example, the bridge electrode 330 may be disposed in a bar shape. In detail, the bridge electrodes 330 may be spaced apart from each other by a predetermined interval on the active area AA, so that the bridge electrodes 330 are disposed in a bar shape.

An insulating material 350 may be disposed on the bridge electrode 330. In detail, the insulating material 350 may be partially disposed on the bridge electrode 330, and a part of the bridge electrode 330 may be covered by the insulating material 350. For example, when the bridge electrode is formed in a bar shape, the insulating material 350 may be disposed on the area except for one end and the opposite end, that is, both ends of the bridge electrode 330.

The first sensing electrodes 310 may be connected to each other and extend on the insulating material 350. For example, the first sensing electrodes 310 extending in the first direction may be connected to each other on the insulating material 350.

In addition, the second sensing electrode 320 may be connected to the bridge electrode 330. In detail, the second sensing electrodes 320 spaced apart from each other may be connected to the bridge electrodes 330, such that the second sensing electrodes 320 may extend in the second direction.

Thus, the first and second sensing electrodes 310 and 320 may be prevented from being short-circuited with each other by the bridge electrode 330 and may be electrically connected to each other, respectively.

The sensing electrode 300 may be connected to the wire electrode 400. In detail, the wire electrode 400 may include a first wire electrode 410 connected to the first sensing electrode 310 and a second wire electrode 420 connected to the second sensing electrode 320.

Meanwhile, the sensing electrode 300 may include a transparent conductive material that allows electricity to flow therethrough without interrupting transmission of light. For example, the sensing electrode may include metal oxide such as indium tin oxide (ITO), indium zinc oxide (IZO), copper oxide, tin oxide, zinc oxide, or titanium oxide.

Alternatively, the sensing electrode 200 may include a nanowire, a photosensitive nanowire film, a carbon nanotube (CNT), graphene, conductive polymer or a mixture thereof.

Alternatively, the sensing electrode 300 may include various metals. For example, the sensing electrode 300 may include at least one of Cr, Ni, Cu, Al, Ag, Mo, Au, Ti and the alloy thereof. In this case, the sensing electrode 300 (or the wire electrode 400) may be formed in a mesh shape. In detail, the sensing electrode 300 may include a plurality of sub-electrodes which are disposed in a mesh shape while alternating with each other.

In detail, the sensing electrode 300 may include mesh lines formed by a plurality of sub-electrodes crossing each other in a mesh shape and mesh opening parts formed between the mesh lines. The mesh opening part may be formed in various shapes. For example, the mesh opening part may have various shapes such as a polygonal shape including a rectangular shape, a diamond shape, a pentagon shape or a hexagonal shape, or a circular shape. In addition, the mesh opening part may be formed in a regular or random shape.

Since the sensing electrode 300 has a mesh shape, even though the sensing electrode 300 is formed of metal, the pattern may be made not to be viewed. The sensing electrode 300 has low electric resistance so that it may be advantageous to the application of the sensing electrode 300 to a sensor for a large-area vehicle.

The first and second wire electrodes 410 and 420 may include a conductive material. For example, the wire electrode 400 may include a material the same as or similar to that of the sensing electrode 300 described above.

The wire electrode 400 may allow the sensing electrode 300 and the printed circuit board 500 to be electrically connected to each other.

The printed circuit board 500 may be configured to transmit the sensing signal of the sensing electrode 300 to a control unit. In detail, the sensing signal of the sensing electrode 300 may be transmitted to the printed circuit board 500 through the wire electrode 400 and the printed circuit board 500 may transmit the sensing signal to the control unit.

Figure 2:
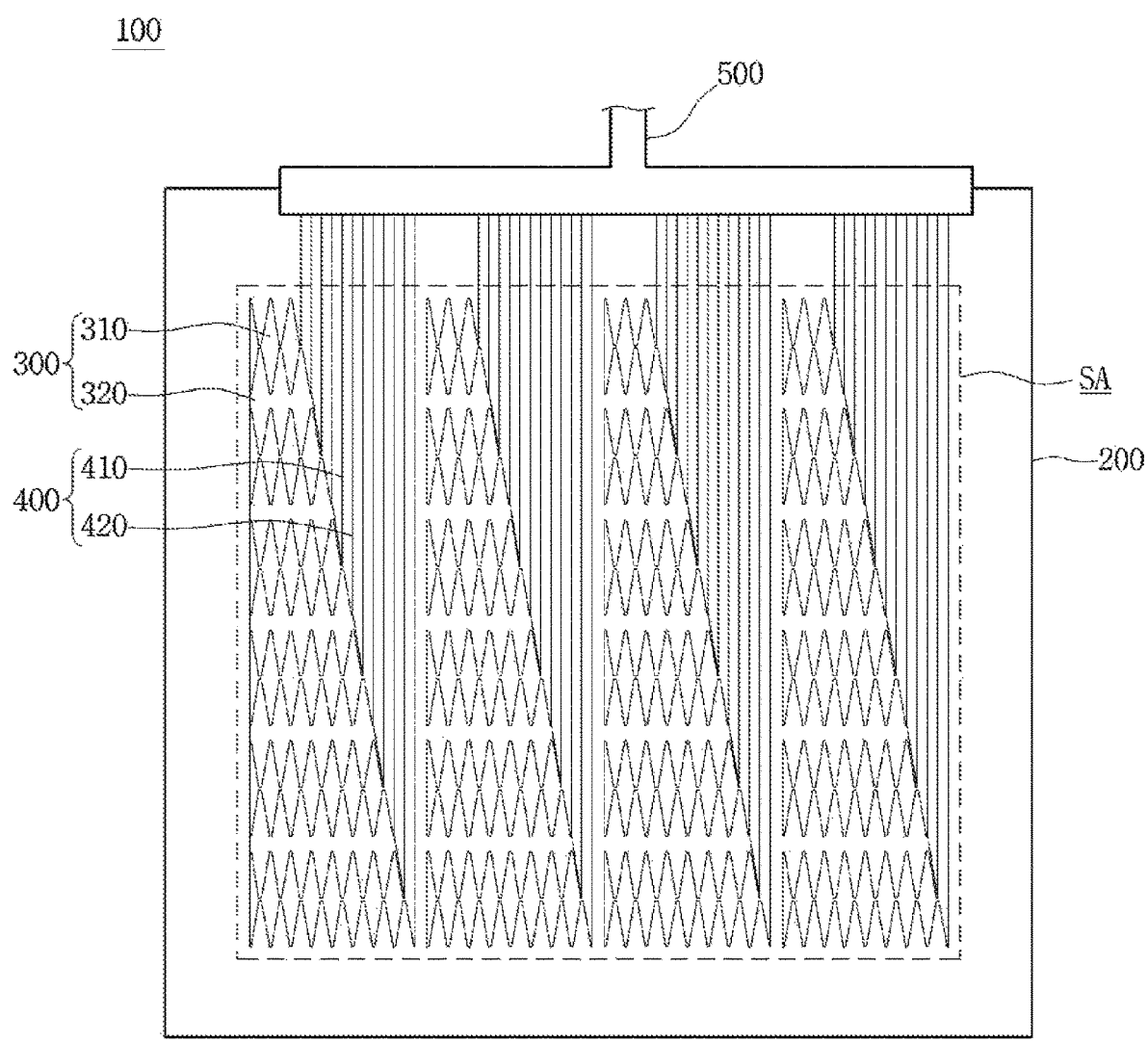
FIG. 2 is a plan view showing a sensor for a vehicle according to another embodiment.

FIG. 2 is a plan view showing a sensor for a vehicle according to another embodiment.

Hereinafter, a sensor for a vehicle according to another embodiment will be described with reference to FIG. 2. In the following description, the description overlapping with that of the sensor for a vehicle according to the embodiment described above will be omitted. The same reference numerals will be assigned to the same or similar elements.

Referring to FIG. 2, a sensor for a vehicle according to another embodiment may include a substrate 200, a sensing electrode 300 and a wire electrode 400. The sensing electrode 300 may include first and second sensing electrode 310 and 320.

The substrate 200 may include a sensing area SA.

The first and second sensing electrodes 310 and 320 may be disposed on the sensing area SA of the same surface of the substrate 200 while being spaced apart from each other.

For example, the first and second sensing electrode 310 and 320 may include a plurality of electrode patterns. The electrode patterns may be arranged in a matrix form.

In detail, the electrode patterns of the first sensing electrode 310 may be spaced apart from those of the second electrode 320 to form pairs of electrode patterns, so that the pairs of electrode patterns may be arranged in a matrix form. That is, all the sensing electrodes according to another embodiment may be disposed on the same surface to have a single-layer structure. When the sensor for a vehicle having the single-layer structure is disposed on a vehicle glass, the sensor has an advantage of sensing raindrops on upper and lower surfaces of the glass at the same time.

For example, the first and second sensing electrodes 310 and 320 may be disposed on the same surface of the substrate 200 while being spaced apart from each other, such that the first and second sensing electrodes 310 and 320 do not make contact with each other. As shown in FIG. 2, the plurality of first and second sensing electrodes 310 and 320 may be alternate with each other in a vertical direction. At least two rows, in which the first and second sensing electrodes 310 and 320 alternate with each other, may be spaced apart from each other by a predetermined interval.

The sensing electrode 300 may have a regular shape such as a rectangular shape or a pentagon shape, or a random shape.

As shown in FIG. 2, each of the first and second sensing electrodes 310 and 320 may include a branch electrode. The branches of the first sensing electrode 310 may be engaged with those of the second electrode 320. Thus, the lengths of sides of the first and second sensing electrodes 310 and 320 that face each other may be increased so that the sensibility may be improved.

The sensing electrodes 300 may be connected to the wire electrodes 400, respectively. That is, the first sensing electrodes 310 may be connected to the first wire electrodes 410, respectively. In addition, the second sensing electrodes 320 may be connected to the second wire electrodes 420, respectively.

In addition, as shown in the drawings, according to the sensor for a vehicle, an external substrate, in which the first sensing electrode 310 having a first directional property is formed, may be spaced apart from an internal substrate in which the second sensing electrode 320 having a second directional property is formed.

Hereinafter, the structure, in which a sensor for a vehicle according to an embodiment is installed on a vehicle, will be described with reference to FIGS. 3 to 7.

Figure 3:
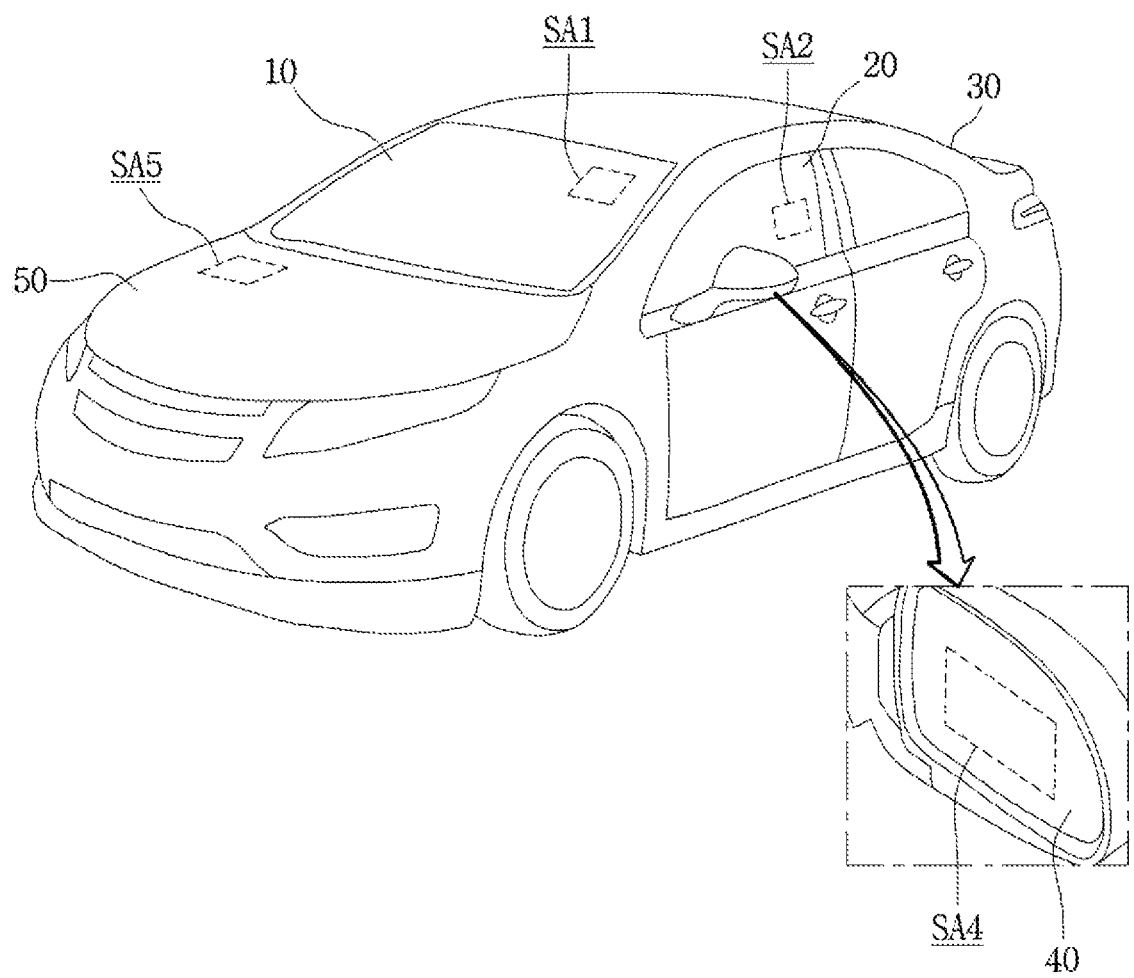
FIG. 3 is a view showing an area of a vehicle to which a sensor for a vehicle is installable.
Figure 4:
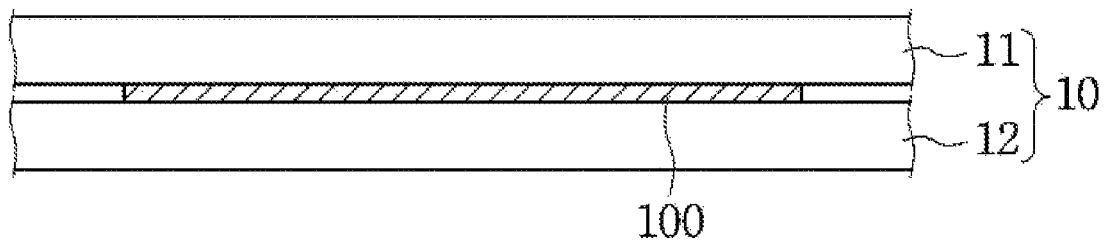
FIG. 4 is a schematic sectional view showing a sensor for a vehicle installed to a vehicle according to one embodiment.
Figure 5:
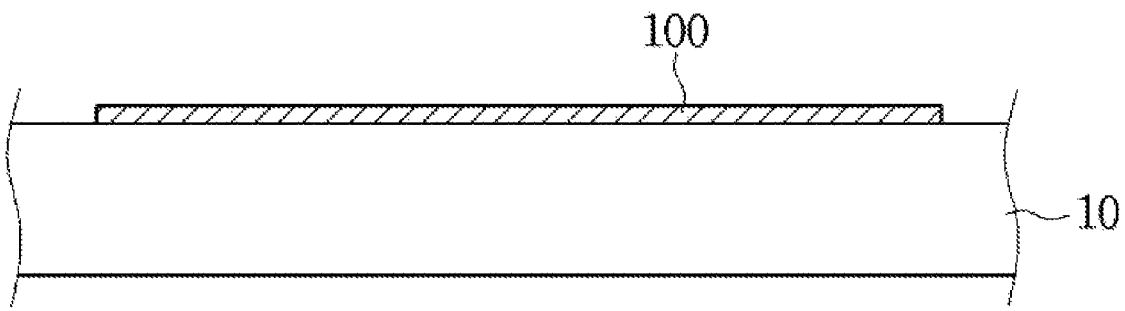
FIG. 5 is a schematic sectional view showing a sensor for a vehicle provided to a vehicle according to another embodiment.
Figure 6:
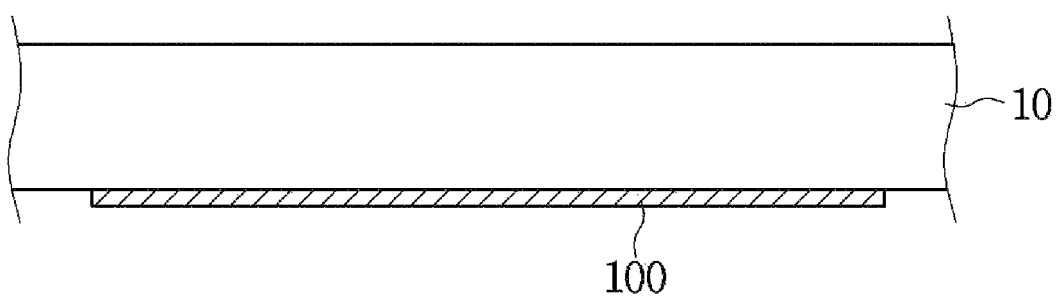
FIG. 6 is a schematic sectional view showing a sensor for a vehicle installed to a vehicle according to still another embodiment.
Figure 7:
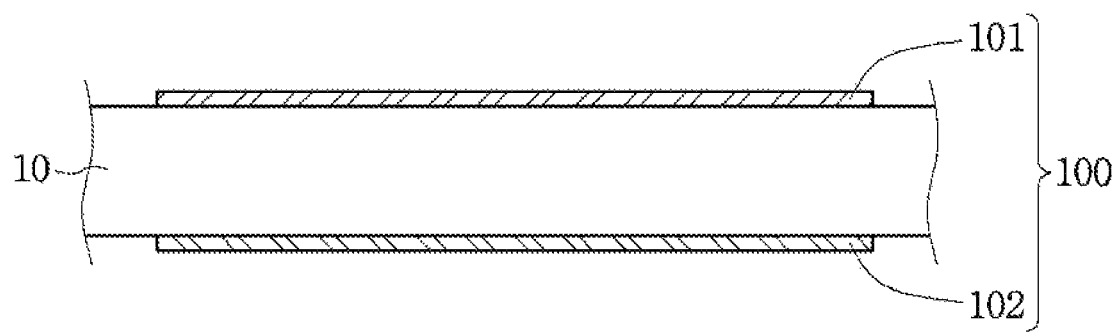
FIG. 7 is a schematic sectional view showing a sensor for a vehicle installed to a vehicle according to still another embodiment.

FIG. 3 is a view showing an area of a vehicle to which a sensor for a vehicle is installable. FIG. 4 is a schematic sectional view showing a sensor for a vehicle installed to a vehicle according to one embodiment. FIG. 5 is a schematic sectional view showing a sensor for a vehicle installed to a vehicle according to another embodiment. FIG. 6 is a schematic sectional view showing a sensor for a vehicle installed to a vehicle according to still another embodiment. FIG. 7 is a schematic sectional view showing a sensor for a vehicle installed to a vehicle according to still another embodiment.

Referring to FIG. 3, a vehicle may include a main body 50, a front glass 10, a side glass 20, a rear glass 30 or a side mirror 40 thereof. In addition, at least one sensor for a vehicle may be installed in a local area of the vehicle. Hereinafter, the local area of a vehicle in which the sensor for a vehicle is installed will be defined as a sensing area.

As described above, since the sensing electrode 300 occupying most of the area of the sensor for a vehicle is transparent, even though the sensor is installed at any positions in the vehicle, the driver's vision may not be blocked.

Therefore, the sensor for a vehicle may be disposed on the front glass of a vehicle which corresponds to the first sensing area SA1. In detail, the first sensing area SA1 may be disposed on the front glass 10 of a driver side. In this case, the first sensing area SA1 may be disposed on an outer periphery of the front glass 10 in order to dispose the printed circuit board 500 inside the vehicle.

The sensor for a vehicle of the first sensing area SA1 may exactly sense raindrops and/or moisture of the front glass in front of a driver, so the driver can take necessary steps, such as a wiper operation, based on the sensing result. In addition, since the sensor disposed in the first sensing area SA1 is transparent, the driver's vision is not blocked.

Meanwhile, the sensor for a vehicle may be disposed on the side glass 20 of a vehicle which corresponds to the second sensing area SA2. In detail, the second sensing area SA2 may be disposed on the side glass 20 of a vehicle, which is provided between a driver and the side mirror 40.

Since, the sensor for a vehicle disposed in the second sensing area SA2 is transparent and has a thin thickness, even though the sensor is disposed on the side glass 20 of a vehicle, the driver's vision may not be blocked and the movement of the side glass 20 may not be interrupted.

In addition, the sensor for a vehicle may be disposed on the rear glass of a vehicle which corresponds to the third sensing area SA3.

The sensor for a vehicle of the third sensing area SA3 may exactly sense raindrops and/or moisture of the rear glass of the vehicle, so the driver can take necessary steps, such as a hot-wire operation, based on the sensing result. In addition, since the sensor disposed in the third sensing area SA3 is transparent, the driver's vision is not blocked.

In addition, the sensor for a vehicle may be disposed on the side mirror 40 of a vehicle which corresponds to the fourth sensing area SA4. In detail, the sensor may be disposed on the top or bottom surface of a mirror included in the side mirror 40.

The sensor for a vehicle of the fourth sensing area SA4 may exactly sense moisture of the side mirror 40, so the driver can take necessary steps, such as a hot-wire operation based on the sensing result. In addition, since the sensor disposed in the fourth sensing area SA4 is transparent, the driver's vision is not blocked.

Lastly, the sensor for a vehicle may be disposed on the main body 50 of a vehicle which corresponds to the fifth sensing area SA5.

As described above, the sensor for a vehicle may be disposed on a vehicle glass. For the purpose of convenience of description, the following description will be focused on the case that the sensor for a vehicle is disposed on the front glass of a vehicle.

In detail, referring to FIG. 4, the vehicle glass 10 may include an outer glass 11 disposed toward the outside of a vehicle and an inner glass 12 disposed toward the inside of the vehicle. The sensor 100 for a vehicle may be interposed between the outer and inner glasses 11 and 12.

In detail, the sensor 100 for a vehicle may be combined with the inner glass 12 with adhesive and the inner and outer glasses 12 and 11 may be combined with each other with adhesive, so that the sensor 100 may be embedded in the vehicle glass 10.

As described above, the sensor 100 for a vehicle disposed in the vehicle glass 10 may sense a raindrop on the outer glass 11.

Alternatively, the sensor 100 for a vehicle may sense the dew formed on the inner glass 12 due to moisture.

Alternatively, the sensor 100 for a vehicle may simultaneously sense the raindrop on the outer glass 11 and the dew on the inner glass 12. In this case, the sensing electrode 300 of the sensor for a vehicle may be provided in a single layer.

Referring to FIG. 5, the sensor 100 for a vehicle may be disposed on the vehicle glass 10. In detail, the sensor 100 for a vehicle may be disposed on the top surface of a vehicle glass 10 which is toward an outside of the vehicle. In more detail, the sensor 100 for a vehicle may make direct contact with the top surface of the vehicle glass 10.

A protective cover may be disposed on the sensor 100 for a vehicle. For example, an optical isotropic film may cover the top and side surfaces of the sensor 100 for a vehicle.

As described above, the sensor 100 for a vehicle disposed on the top surface of the vehicle glass 10 may sense a raindrop on the outer glass 11.

Referring to FIG. 6, the sensor 100 for a vehicle may be disposed on the vehicle glass 10. In detail, the sensor 100 for a vehicle may be disposed on the bottom surface of the vehicle glass 10 which is toward the inside of the vehicle. In more detail, the sensor 100 for a vehicle may make direct contact with the bottom surface of the vehicle glass 10.

The protective cover may be disposed on the sensor 100 for a vehicle. In detail, the protective cover may cover the sensor 100 for a vehicle. For example, an optical isotropic film may be used as the protective cover.

As described above, the sensor 100 for a vehicle disposed on the bottom surface of the vehicle glass 10 may sense dew on the bottom surface of the vehicle glass 10.

Referring to FIG. 7, the sensor 100 for a vehicle may include an outer vehicle sensor 101 disposed on the top surface of the vehicle glass 10 and an inner vehicle sensor 102 disposed on the bottom surface of the vehicle glass 10. In this case, the outer and inner vehicle sensors 101 and 102 may share a printed circuit board 500 and/or a control unit.

As described above, the outer vehicle sensor 101 disposed on the top surface of the vehicle glass 10 may sense a raindrop on the outer glass 11. The inner vehicle sensor 102 disposed on the bottom surface of the vehicle glass 10 may sense dew on the bottom surface of the vehicle glass 10.

Hereinafter, a principle and a process of sensing a raindrop by the sensor 100 for a vehicle will be described with reference to FIGS. 8 to 10.

Figure 8:
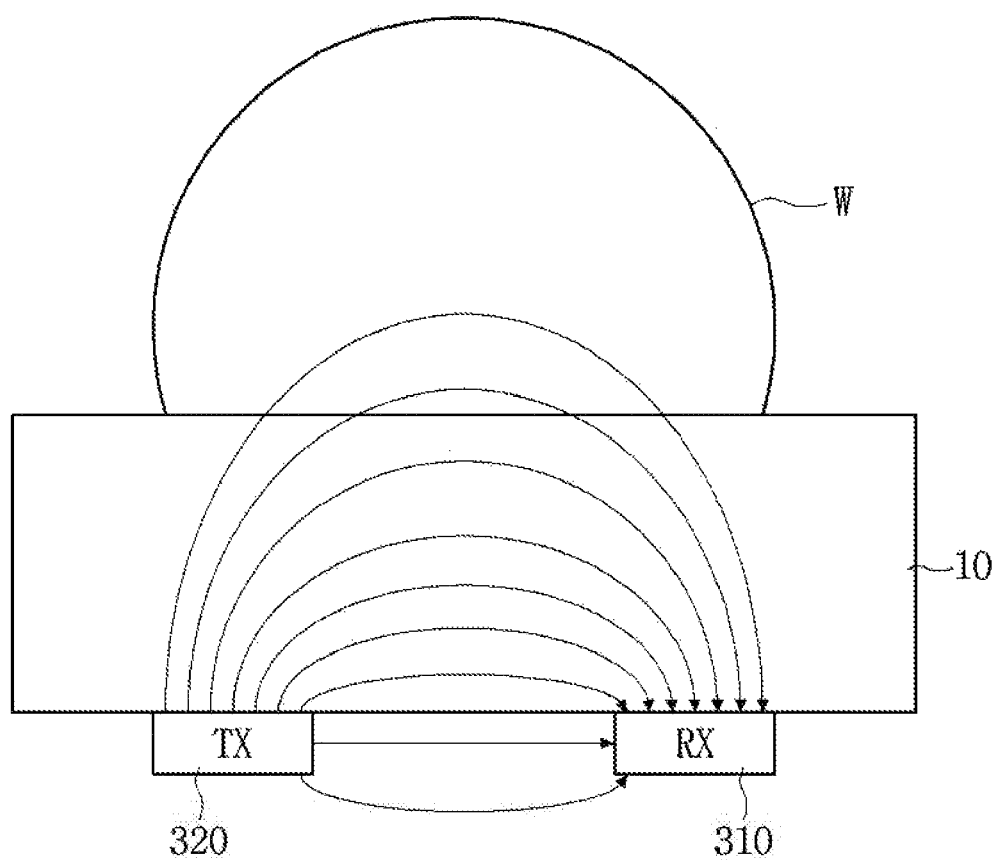
FIGS. 8 and 9 are views illustrating a principle of sensing a raindrop by the sensor for a vehicle according to an embodiment.
Figure 9:
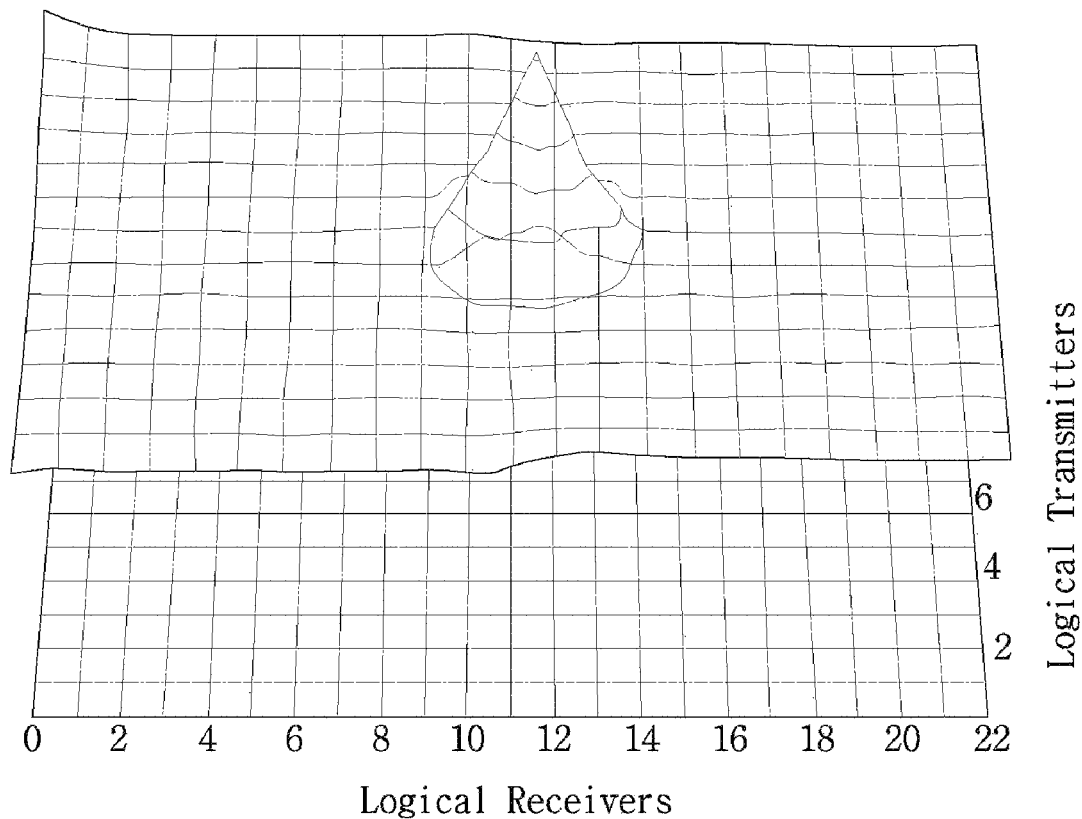

FIGS. 8 and 9 are views illustrating a principle of sensing a raindrop by the sensor 100 for a vehicle according to an embodiment. FIG. 10 is a flowchart illustrating a method of sensing a raindrop by the sensor 100 for a vehicle according to an embodiment.

First, one of the first and second sensing electrodes 310 and 320 may serve as a driving electrode to which a driving signal is applied. One of the first and second sensing electrodes 310 and 320 may serve as a sensing electrode from which transmits a sensing signal to the control unit.

For example, the control unit may include a driving unit which applies a driving signal to the second sensing electrode 320 serving as the driving electrode.

When the driving signal is applied to the second sensing electrode 320, the first and second sensing electrodes 310 and 320 may be capacitively coupled to each other, so that mutual capacitance may be formed.

When a raindrop W is provided on the sensing electrode 300 as shown in FIG. 8, a portion of the mutual capacitance passes through the raindrop W to be coupled, so that the capacitance may vary between the sensing electrodes 300 on which the raindrop W is provided as shown in FIG. 9.

The control unit may receive a signal corresponding to the capacitance variation from the first or second sensing electrode 310 or 320. For example, the control unit may include a sensing unit which receives the signal corresponding to the varied capacitance from the first sensing electrode 310 serving as a sensing electrode.

The control unit may sense a raindrop W through the signal corresponding to the varied capacitance.

The sensor 100 for a vehicle may not only sense a raindrop W, but also measure rainfall. In detail, when rainfall is heavy, a great amount of raindrops may be provided on the sensing electrode 300 of the sensor 100 for a vehicle, so that the capacitance of the sensing electrode 300 disposed at the front of the sensor 100 for a vehicle may vary. That is, since the capacitance variation area is proportional to an amount of rainfall, the control unit may measure the rainfall by analyzing the capacitance variation.

Figure 10:
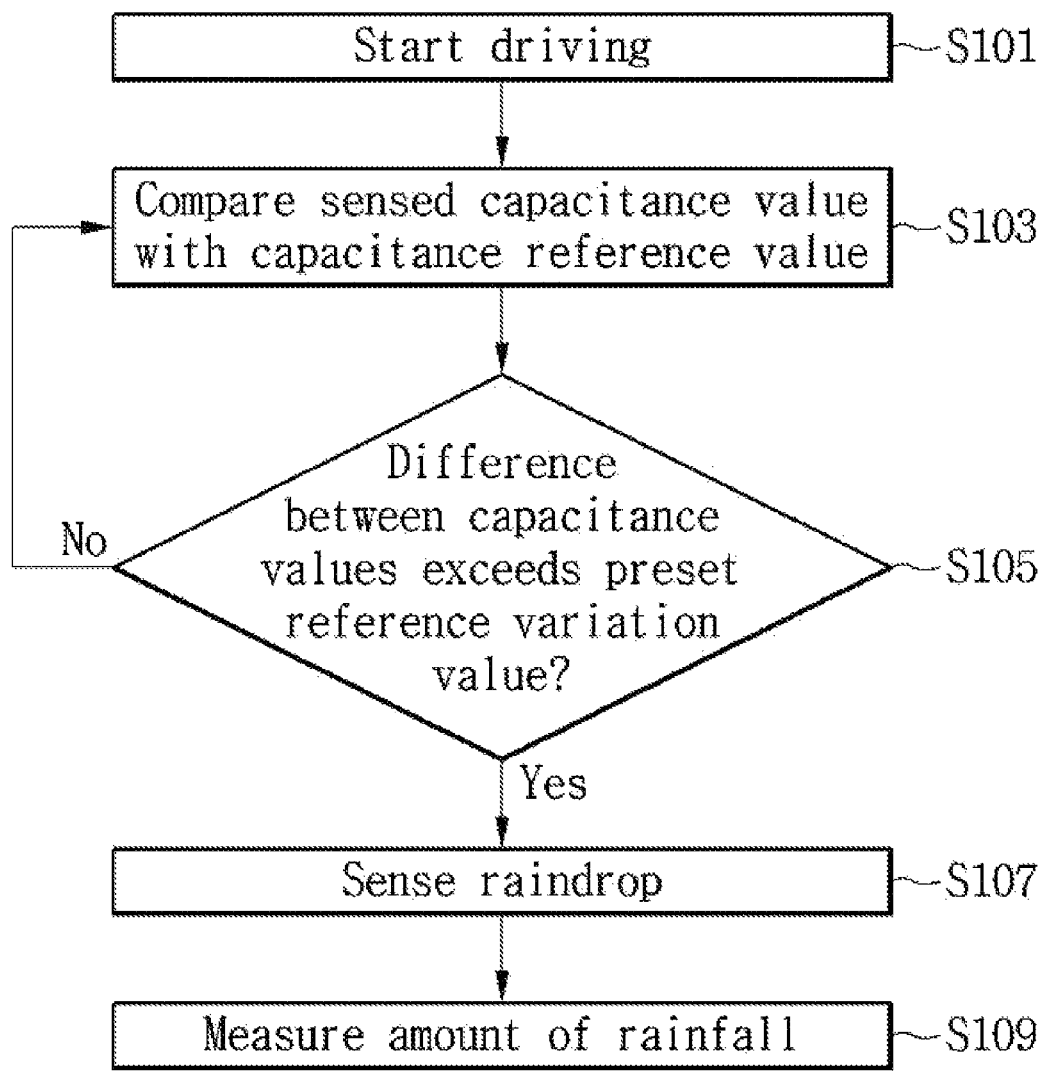
FIG. 10 is a flowchart illustrating a method of sensing raindrops by a sensor for a vehicle according to an embodiment.

In more detail, referring to FIG. 10, when driving is started, the control unit may drive the sensor 100 for a vehicle in step S101. In this case, the control unit may set a capacitance value transmitted from the sensor 100 for a vehicle as a capacitance reference value. Alternatively, the capacitance reference value of the sensor 100 for a vehicle may be set as a default value.

In step S103, the control unit may continuously receive the capacitance value from the sensor 100 for a vehicle, and compare the capacitance value with the capacitance reference value when the capacitance value is changed.

In steps S105 and S107, when a difference between capacitance values exceeds a preset amount of a capacitance variation, the control unit may operate as a case that a raindrop is provided on the vehicle glass 10.

In step S109, the control unit may measure an amount of rainfall based on an area of the sensing electrode 300 exceeding the amount of the capacitance variation.

Then, if the raindrop is removed from the vehicle glass 10 through an operation such as a wiper operation according to the amount of rainfall, the control unit may continuously measure the amount of rainfall while resetting the capacitance reference value.

Hereinafter, a principle and a process of sensing moisture by the sensor 100 for a vehicle will be described with reference to FIGS. 11 and 12.

Figure 11:
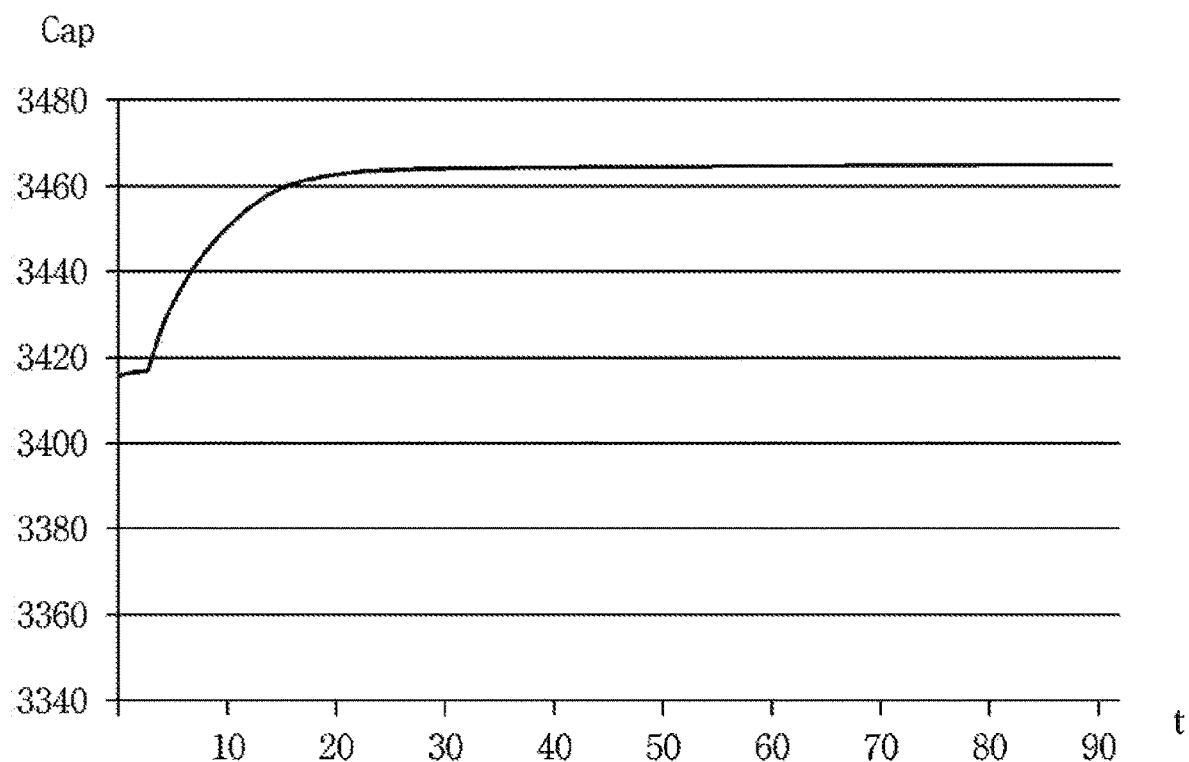
FIG. 11 is a graph showing a result of measuring a variation of mutual capacitance after disposing a sensor for a vehicle according to an embodiment in a high-temperature, high-humidity chamber.

FIG. 11 is a graph showing a result of measuring a variation of mutual capacitance after disposing the sensor 100 for a vehicle according to an embodiment in a high-temperature, high-humidity chamber. FIG. 12 is a flowchart illustrating a method of sensing moisture by the sensor for a vehicle according to an embodiment.

Referring to FIG. 11, as moisture starts to be condensed on the sensor 100 for a vehicle in the high-temperature, high-humidity chamber, it may be confirmed that the capacitance is changed.

Similarly to a raindrop, a portion of mutual capacitance passes through the dew formed by the moisture on the sensor 100 for a vehicle to be coupled, so that the capacitance may be varied.

The control unit may measure the moisture generated on the vehicle glass 10 by measuring the capacitance variation.

Figure 12:
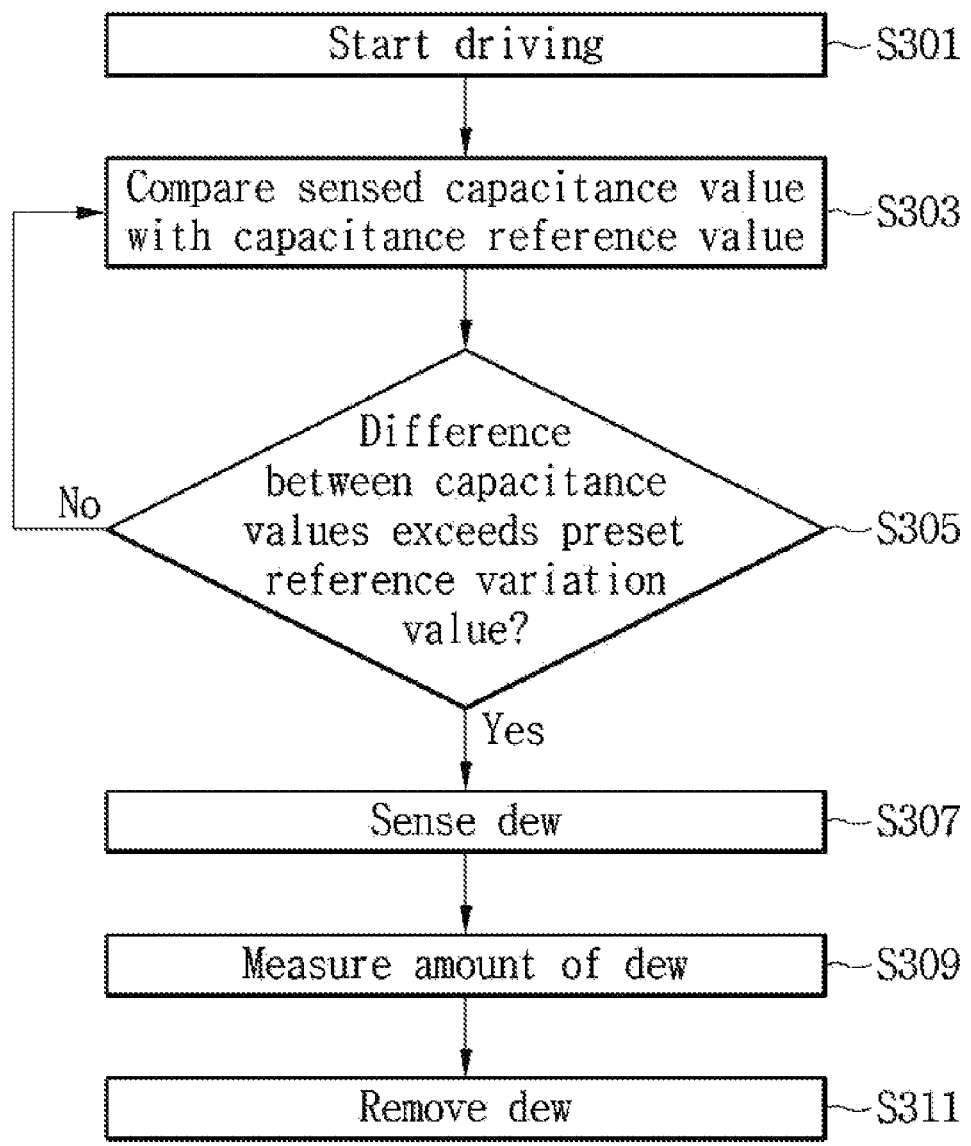
FIG. 12 is a flowchart illustrating a method of sensing moisture by a sensor for a vehicle according to an embodiment.

In more detail, referring to FIG. 12, when driving is started, the control unit may drive the sensor 100 for a vehicle in step S301. In this case, the control unit may set a capacitance value transmitted from the sensor 100 for a vehicle as a capacitance reference value. Alternatively, the capacitance reference value of the sensor 100 for a vehicle may be set as a default value.

In step S303, the control unit may continuously receive the capacitance value from the sensor 100 for a vehicle, and compare the capacitance value with the capacitance reference value when the capacitance value is changed.

In steps S305 and 307, when a difference between capacitance values exceeds a preset amount of capacitance variation, the control unit may operate as a case that dew is generated on the vehicle glass 10.

In step S309, the control unit may measure an amount of dew based on the varied capacitance value. That is, a degree of turbidity of the vehicle glass 10 due to the moisture may be measured based on an amount of dew. In this case, the control unit may more exactly measure the degree of turbidity of the vehicle glass 10 due to the moisture by adding a gradient of the capacitance variation as a parameter. In detail, when the degree of turbidity due to moisture is abruptly varied, the control unit may determine that the amount of dew misted by moisture is increased.

Then, in step S311, the control unit may remove the dew from the vehicle glass 10 by using the sensing electrode 300 as a hot-wire. In detail, the control unit may remove the dew from the vehicle glass 10 by using at least one of the first and second sensing electrodes 310 and 320 as a hot-wire through the driving unit.

For example, the control unit may use the first sensing electrode 310 which is a sensing electrode as a hot-wire through the driving unit. In this case, the first sensing electrode 310 may be formed of a metal having a mesh shape.

That is, the control unit may exactly measure an amount of dew due to moisture through the sensing electrode 300 and remove the dew by using the sensing electrode 300 as a hot-wire, so that the driver's convenience may be achieved.

Figure 13:
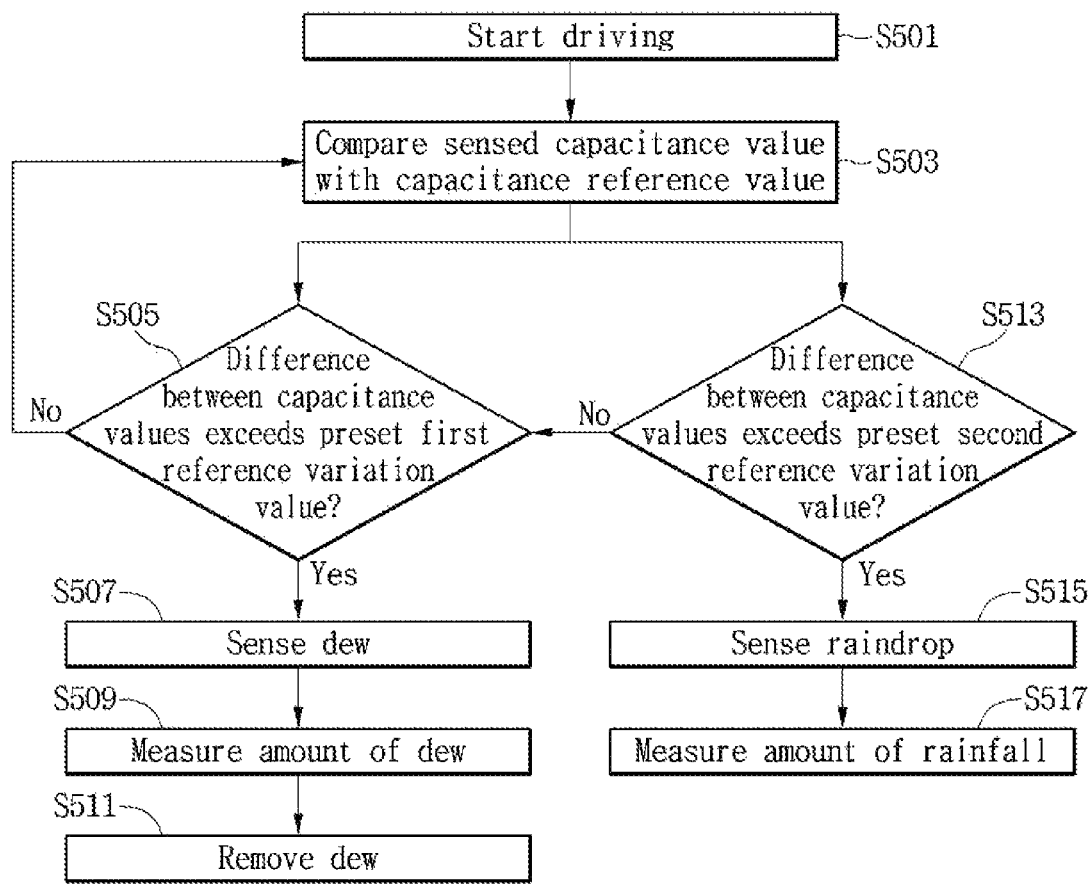
FIG. 13 is a flowchart illustrating a hybrid sensing method by a sensor for a vehicle according to an embodiment.

FIG. 13 is a flowchart illustrating a hybrid sensing method by the sensor 100 for a vehicle according to an embodiment.

Referring to FIG. 13, the sensor 100 for a vehicle according to an embodiment may simultaneously sense the raindrop on the outer glass 11 and the dew on the inner glass 12. In this case, the sensor 100 for a vehicle may be embedded in the vehicle glass 10.

In detail, when driving is started, the control unit may drive the sensor 100 for a vehicle in step S501. In this case, the control unit may set a capacitance value transmitted from the sensor 100 for a vehicle as a capacitance reference value. Alternatively, the capacitance reference value of the sensor 100 for a vehicle may be set as a default value.

In step S503, the control unit may continuously receive the capacitance value from the sensor 100 for a vehicle, and compare the capacitance value with the capacitance reference value when the capacitance value is changed.

In steps S505, when a difference between the capacitance reference value and the received capacitance value exceeds a preset first amount of capacitance variation, the control unit may operate as a case that dew is formed on the vehicle glass 10.

In this case, the control unit may more exactly sense the generation of dew through a gradient of the variation of capacitance. That is, when the capacitance variation value is slowly changed to exceed the first amount of capacitance variation, the control unit may operate as a case that dew is formed on the vehicle glass 10.

In addition, the control unit may measure an amount of dew based on the varied capacitance value in step S509. That is, the control unit may measure a degree of turbidity of the vehicle glass due 10 due to moisture based on the amount of dew. In this case, the control unit may more exactly measure the degree of turbidity of the vehicle glass 10 due to the moisture by adding a gradient of the capacitance variation as a parameter.

Then, in step S511, the control unit may remove the dew from the vehicle glass 10 by using the sensing electrode 300 as a hot-wire. In detail, the control unit may remove the dew from the vehicle glass 10 by using at least one of the first and second sensing electrodes 310 and 320 as a hot-wire through the driving unit.

Meanwhile, in steps S513 and 515, when the difference between the capacitance reference value and the received capacitance value exceeds a preset second amount of capacitance variation, the control unit may operate as a case that a raindrop is formed on the vehicle glass 10.

The second amount of capacitance variation may be greater than the first amount of capacitance variation because the value of capacitance variation varied with the raindrop is great.

The control unit may more exactly sense the generation of the raindrop based on the gradient of the capacitance variation. That is, when the value of capacitance variation is abruptly varied to exceed the first amount of capacitance variation, the control unit may operate as a case that a raindrop is formed on the vehicle glass 10.

In addition, in step S517, the control unit may measure an amount of rainfall based on an area of the sensing electrode 300 exceeding the amount of the capacitance variation. Then, if the raindrop is removed from the vehicle glass 10 through an operation such as a wiper operation according to the amount of rainfall, the control unit may continuously measure the amount of rainfall while resetting the capacitance reference value.

Hereinafter, a vehicle system to which the sensor 100 for a vehicle according to the embodiment described above is applied will be described.

Figure 14:
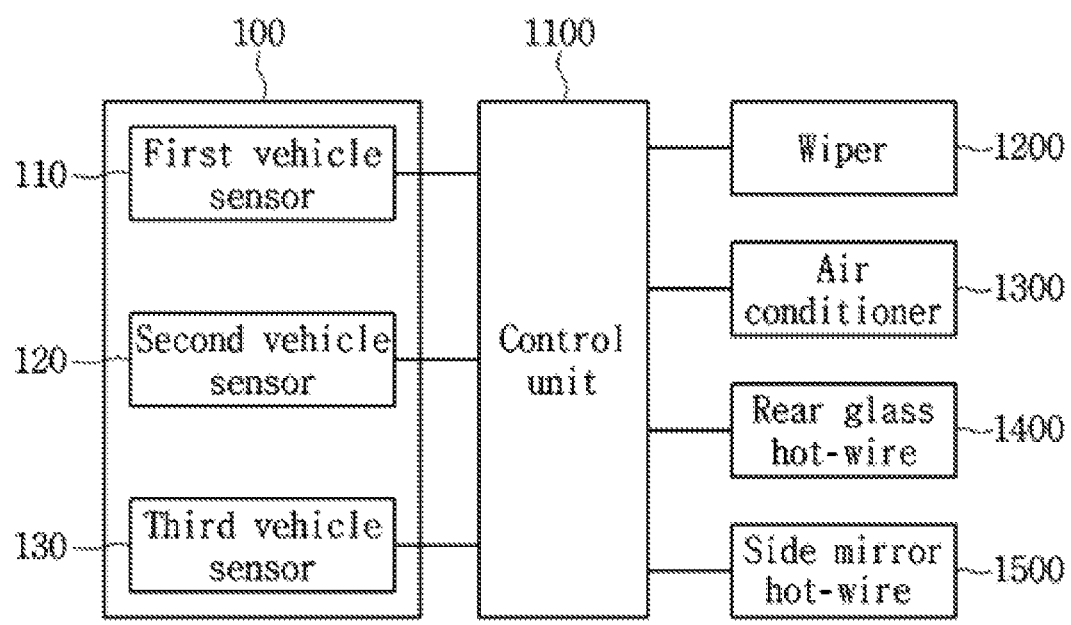
FIG. 14 is a block diagram showing a vehicle system according to an embodiment.

FIG. 14 is a block diagram showing a vehicle system according to an embodiment.

Referring to FIG. 14, a vehicle system according to an embodiment includes a sensor 100 for a vehicle, a wiper 1200, an air conditioner 1300, a rear glass hot-wire 1400, a side mirror hot-wire 1500 and a control unit 1100.

First, at least one sensor 100 for a vehicle may be included therein.

In detail, a first vehicle sensor 110 may be disposed on the vehicle front glass 10 to sense moisture, a mist and a raindrop on the vehicle front glass 10. In addition, a second vehicle sensor 120 may be disposed on the vehicle rear glass 30 to sense moisture and a mist on the vehicle rear glass 30. Further, a third vehicle sensor 130 may be disposed on the side mirror 40 to sense moisture and a mist on the side mirror 40.

As described above, the sensing signal of the sensor 100 for a vehicle may be transmitted to the control unit 1100.

The control unit 1100 may automatically operate at least one of the wiper 1200, the air conditioner 1300 and the hot-wire.

In detail, when the control unit 1100 receives the sensing signal corresponding to the raindrop and rainfall through the first vehicle sensor 110, the control unit 1100 may automatically operate the wiper 1200 according to the sensing signal. In this case, the speed of the wiper 1200 may be proportional to the amount of rainfall.

In addition, when the control unit 1100 receives the sensing signal corresponding to the moisture and the amount of dew through the first vehicle sensor 110, the control unit 1100 may operate the air conditioner 1300 according to the sensing signal. For example, the control unit 1100 may allow cool air to be blown to the vehicle front glass 10 by using the air conditioner 1300, so that dew may be prevented from being generated or the generated dew may be removed.

In addition, when the control unit 1100 receives the sensing signal corresponding to the moisture and the amount of dew through the second vehicle sensor 120, the control unit 1100 may operate the rear glass hot-wire 1400 according to the sensing signal, so that the dew may be removed. In this case, the rear glass hot-wire 1400 may be the sensing electrode 300 of the sensor 100 for a vehicle, but the embodiment is not limited thereto.

In addition, when the control unit 1100 receives the sensing signal corresponding to the moisture and the amount of dew through the third vehicle sensor 130, the control unit 1100 may operate the side mirror hot-wire 1500 according to the sensing signal, so that the dew may be removed. In this case, the side mirror hot-wire 1500 may be the sensing electrode 300 of the sensor 100 for a vehicle, but the embodiment is not limited thereto.

That is, according to the vehicle system of an embodiment, the transparent sensor 100 for a vehicle is suitably disposed at a position required by a vehicle, so that the vehicle system may exactly measure information required to secure driver's sight. In addition, driver's convenience may be improved by suitably controlling a wiper or hot-wire based on the information collected by the sensor 100 for a vehicle.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

INDUSTRIAL APPLICABILITY

The sensor for a vehicle according to an embodiment may be installed to an internal combustion engine vehicle, a hybrid vehicle, an electric vehicle, a motorcycle, a ship, an airplane and a train including an engine as a power source to exactly sense dew or raindrops, so that the sensor is industrially applicable.

The invention claimed is:

1. A sensor for determining a raindrop or a mist on a vehicle, the sensor comprising:
   a sensing electrode disposed on a glass of the vehicle;
   a wire electrode connected to the sensing electrode;
      wherein the sensing electrode comprises a first sensing electrode and a second sensing electrode spaced apart from the first sensing electrode,
      wherein the first sensing electrode, the second sensing electrode and the wire are formed of a metal,
   a control unit including a driving unit and a sensing unit,
      wherein the driving unit of the control unit applies a driving signal to the second sensing electrode, and the first sensing electrode provides a sensing signal to the sensing unit of the control unit, wherein the control unit to determine a variation of capacitance based on the sensing signal, and
      wherein the driving unit to provide power to the first sensing electrode such that the first sensing electrode is a hot-wire to apply heat.

2. The sensor of claim 1, wherein the first sensing electrode extends in a first direction, and the second sensing electrode extends in a second direction, and
   the sensor further comprises an insulating material interposed between the first and second sensing electrodes.

3. The sensor of claim 1, wherein each of the first and second sensing electrodes includes a plurality of electrode patterns, and
   the electrode patterns of the first sensing electrode are spaced apart from the electrode patterns of the second sensing electrode.

4. The sensor of claim 1, wherein the glass of the vehicle includes at least one of a front glass of the vehicle, a side glass of the vehicle, a rear glass of the vehicle and a side mirror.

5. The sensor of claim 1, wherein the glass of the vehicle includes an outer glass and an inner glass disposed on the outer glass, and
   the sensor further comprises a substrate interposed between the outer and inner glasses.

6. The sensor of claim 1, further comprising a substrate making direct contact with top and bottom surfaces of a local area of the glass of the vehicle.

7. The sensor of claim 1, wherein the sensing electrode senses a raindrop provided on a top surface of the glass of the vehicle based on a variation of capacitance.

8. The sensor of claim 1, wherein the sensing electrode senses dew provided on a bottom surface of the glass of the vehicle based on a variation of capacitance.

9. The sensor of claim 1, further comprising a substrate disposed between the glass of the vehicle and the sensing electrode,
   wherein the sensing electrode is formed on the substrate.

10. The sensor of claim 9, wherein the substrate is bent to have a curved surface.

11. The sensor of claim 1, wherein the first sensing electrode and the second sensing electrode are in direct physical contact with the glass of the vehicle.

12. The sensor of claim 5, wherein the first sensing electrode and the second sensing electrode are in direct physical contact with the outer glass and the inner glass.

13. The sensor of claim 5, wherein the inner and outer glasses are combined with each other with adhesive, and
   wherein the sensing electrode is embedded in the glass of the vehicle.

14. The sensor of claim 1, wherein the sensing electrode simultaneously senses the raindrop and the dew.

* * * * *